US008127882B2

(12) United States Patent
Johnson et al.

(10) Patent No.: US 8,127,882 B2
(45) Date of Patent: Mar. 6, 2012

(54) SECURITY DEVICE

(76) Inventors: William Neville Heaton Johnson, St. Peter Port (GB); Christopher J. A. Glynn, Standlake (GB)

(*) Notice: Subject to any disclaimer, the term of this patent is extended or adjusted under 35 U.S.C. 154(b) by 762 days.

(21) Appl. No.: 11/628,812

(22) PCT Filed: Jun. 9, 2005
(Under 37 CFR 1.47)

(86) PCT No.: PCT/GB2005/002295
§ 371 (c)(1),
(2), (4) Date: Oct. 20, 2008

(87) PCT Pub. No.: WO2005/120878
PCT Pub. Date: Dec. 22, 2005

(65) Prior Publication Data
US 2011/0127101 A1    Jun. 2, 2011

(30) Foreign Application Priority Data
Jun. 9, 2004  (GB) .................................. 0412879.9
Jun. 14, 2004 (GB) .................................. 0413219.7

(51) Int. Cl.
*B60R 25/04* (2006.01)
(52) U.S. Cl. ........ 180/287; 180/272; 307/10.6; 382/117
(58) Field of Classification Search .................. 180/287, 180/272; 301/10.1–10.6; 382/117; 307/10.1–10.6
See application file for complete search history.

(56) References Cited

U.S. PATENT DOCUMENTS

| 2,794,089 | A | * | 5/1957 | Hogg et al. ................. 200/85 R |
| 4,996,161 | A | * | 2/1991 | Conners et al. ............... 436/132 |
| 5,106,184 | A |   | 4/1992 | Milbocker et al. |
| 5,291,560 | A | * | 3/1994 | Daugman ..................... 382/117 |
| 5,686,765 | A | * | 11/1997 | Washington ................. 307/10.5 |
| 5,845,733 | A |   | 12/1998 | Wolfsen et al. |
| 5,867,587 | A | * | 2/1999 | Aboutalib et al. ............ 382/117 |
| 6,097,295 | A | * | 8/2000 | Griesinger et al. ........... 340/576 |
| 6,167,746 | B1 | * | 1/2001 | Gammenthaler ............ 73/19.01 |
| 6,661,345 | B1 | * | 12/2003 | Bevan et al. ................. 340/575 |
| 6,726,636 | B2 | * | 4/2004 | Der Ghazarian et al. ..... 600/532 |

(Continued)

FOREIGN PATENT DOCUMENTS

| DE | 19803158 | 5/1999 |
| DE | 19830541 | 1/2000 |
| EP | 0589191 | 3/1994 |

(Continued)

*Primary Examiner* — Drew Brown
(74) *Attorney, Agent, or Firm* — The Webb Law Firm, PC

(57) ABSTRACT

A security device for a means of transport comprising a radiation source to direct radiation into the eye of a person intending to take control of the means of transport, so that the radiation is internally reflected within the eye and emerges from the eye with a substantial spectral content corresponding to the spectral content of food flowing through the retina of the eye, and a receiver arrangement to receive the radiation emanating from the eye of the person and to perform a spectral analysis of the reflected radiation to determine the concentration of at least one chemical within the blood of the person, the device further comprising an alarm unit to generate an alarm and/or an immobilizer unit to immobilize the means of transport, the or each unit being responsive to the said determination of concentration when the concentration of the said chemical is outside a permitted threshold range. Preferably, radiation is transmitted to the retina, and the spectral analysis is carried out for radiation reflected from the retina.

21 Claims, 1 Drawing Sheet

U.S. PATENT DOCUMENTS

| | | | |
|---|---|---|---|
| 7,299,890 B2 * | 11/2007 | Mobley et al. | 180/272 |
| 2002/0122572 A1 * | 9/2002 | Seal et al. | 382/117 |
| 2004/0012261 A1 | 1/2004 | Albert | |
| 2004/0202354 A1 * | 10/2004 | Togino | 382/117 |

FOREIGN PATENT DOCUMENTS

| | | |
|---|---|---|
| GB | 2313154 | 11/1997 |
| GB | 2322956 | 9/1998 |
| WO | 99/32317 | 7/1999 |

* cited by examiner

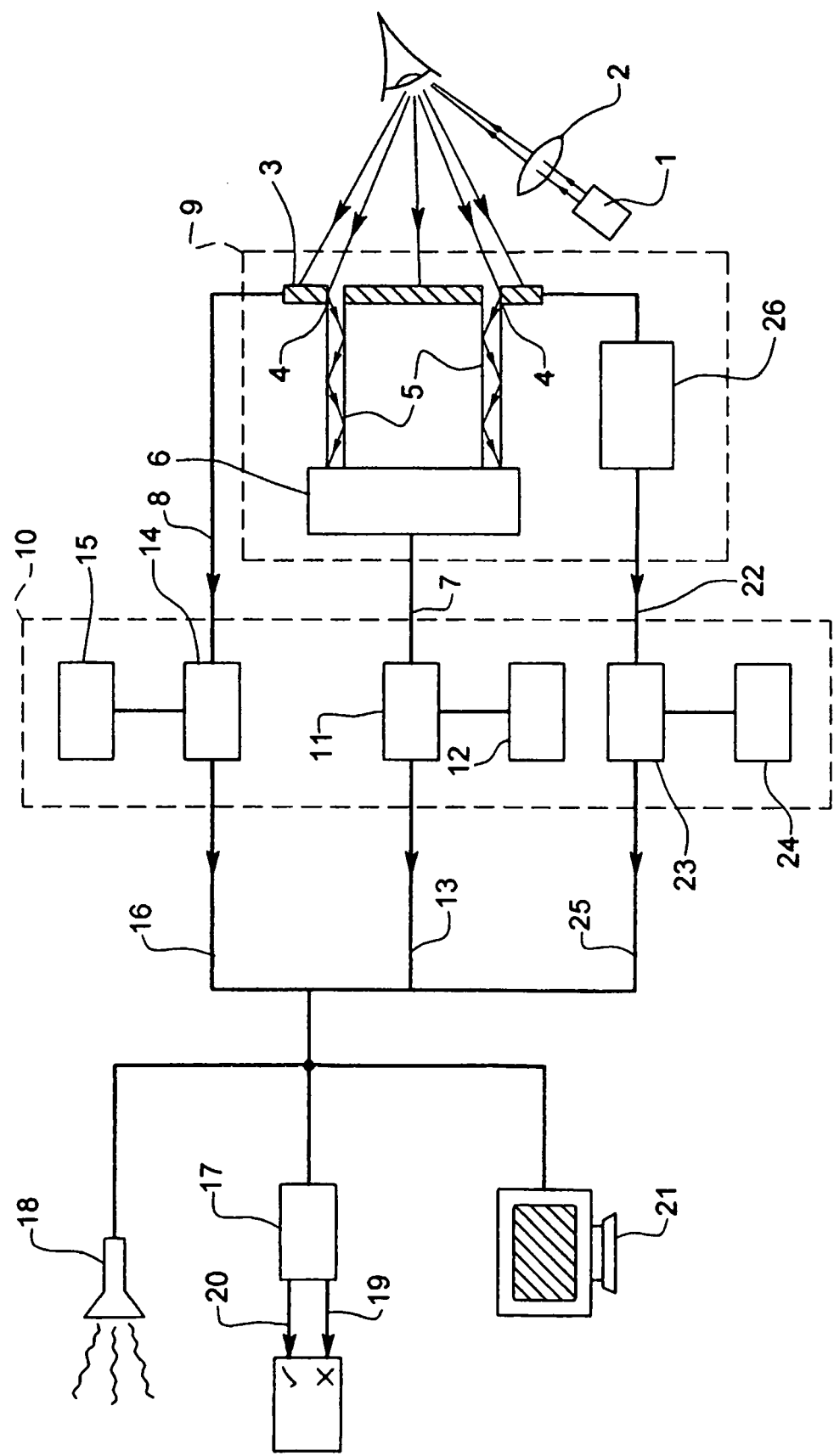

SECURITY DEVICE

DESCRIPTION OF INVENTION

THE PRESENT INVENTION relates to a security device for a means of transport. In particular the invention relates to a security device mounted to a road vehicle such as a car or the like, lorry, truck, coach or bus, and aircraft, a hovercraft, a train, ship or boat, or any other means of transport.

It has been proposed before to provide a security device for a vehicle in the form of a device which may be used to check the identity of a person, may be used for determining if a person is intoxicated, and which may be used for determining if a person is drowsy. The security device is arranged to permit the driving of a vehicle only by an appropriate person, confirmed by the checking of the identity of the person, and then only if the person is not intoxicated. The security device provides an alarm should the person driving the vehicle be deemed to be drowsy or sleepy.

A security device of this type is disclosed in WO99/32317. The prior proposed security device incorporates a scanner for scanning the iris of one or both of the eyes of the driver of the vehicle. An image of the or each iris is then obtained compared with stored images of irises belonging to authorised drivers of the vehicle. If the comparison results in a match, the operator is determined to be an authorised driver.

The described arrangement also incorporates intoxication monitoring optics capable of collecting light reflected and emitted from the eye of the vehicle operator, the optics serving to spectrally separate the collected light form an absorbence and fluorescence emission pattern, the spectrally separated light being focussed on to the sensing surface of an optical sensor. The measured pattern formed from the spectrally separate light is compared with stored data sets representative of patterns representative of particular intoxicants or particular combinations of intoxicants, and associated concentrations of the intoxicants in the body. The comparison leads to a determination of whether the vehicle operator is sober or is too intoxicated to drive the vehicle, and this determination must be positive if the engine of the vehicle is to be started.

The prior art Specification teaches that it is light primarily emitted from the tear film and structures of the eye that passes through the intoxication monitoring optics. Consequently the arrangement effectively operates to analyse the concentration of specific intoxicants within the tears present in the eye, and whilst there is a link between the concentration of intoxicants in the tear fluid and the degree of inebriation of a person, the levels of intoxicants present in tears are not conclusively indicative of the degree of inebriation. The present invention, therefore, seeks to provide a security device in which the degree of inebriation of a person can be determined accurately.

According to one aspect of this invention there is provided a security device for a means of transport comprising a radiation source to direct radiation into the eye of a person intending to take control of the means of transport, so that the radiation is internally reflected within the eye and emerges from the eye with a substantial spectral content corresponding to the spectral content of blood flowing through the retina of the eye, and a receiver arrangement to receive radiation emanating from the eye of the person and to perform a spectral analysis of the reflected radiation to determine the concentration of at least one chemical within the blood of the person, the device further comprising an alarm unit to generate an alarm and/or an immobiliser unit to immobilise the means of transport, the or each unit being responsive to the said determination of concentration when the concentration of the said chemical is outside a permitted threshold range.

Preferably the receiver arrangement is configured to form a spectral analysis of the reflected radiation to determine the concentration of alcohol within the blood of the person, the alarm unit being configured to generate an alarm and/or the immobiliser unit being configured to immobilise the means of transport in response to a determination of a concentration of alcohol concentration in excess of a predetermined threshold.

Conveniently the receiver arrangement is configured to perform a spectral analysis of the reflected radiation to determine the concentration of glucose within the blood of the person, the alarm unit being configured to generate an alarm and/or the immobiliser unit being configured to immobilise the means of transport in response to the concentration of glucose being above a predetermined threshold or second beneath a permitted threshold.

Advantageously the radiation source is arranged to provide radiation in sequential pulses, the receiver arrangement being configured to perform said spectral analysis on reflected radiation received during a selected time period relative to each said pulse so as to reduce the proportion of light reflected from the tears, tear film, cornea and/or lens of the eye.

Preferably the receiving means is configured to perform the spectral analysis during a time period which commences at the end of or shortly after the end of each said pulse.

Conveniently the radiation source is configured to focus the radiation in the plane of the pupil of the eye.

Advantageously the radiation source is a source of polarised light and wherein the receiver arrangement is also polarised, the polarisation being such that the receiver will receive only a minimum of light reflected from the tears, tear film, cornea and/or lens of the eye.

Preferably the receiver arrangement is configured to generate at least one data signal indicative of additional biometric information relating to the person, there being a comparator arrangement to compare said data signal with corresponding predetermined signals stored in the memory and to generate at least one output signal, the alarm unit and/or the immobiliser unit being responsive to said output signal.

Conveniently the comparator arrangement includes a recognition device which receives a data signal in the form of an image of at least part of the eye of the person and compares the image with a corresponding predetermined image stored in a memory to verify the identity of the person and generate one of said at least one output signals in the form of a signal indicative of said verification Advantageously the image is an image of at least a portion of the iris of the person.

Preferably the receiver arrangement is configured to determine hippus of the iris of the eye, and to inhibit generation of said output signal if hippus is not present.

Conveniently the receiver arrangement device further comprises a pupillometry device which receives a pupillometry data signal in the form of a series of separate images of the pupil of the person formed by said reflected radiation over a set time period, the pupillometry device being configured to analyse specified information within the pupillometry data signal and generate an output signal in the form of an alertness signal indicative of the level of said mental alertness of said person, being beneath an acceptable threshold, the alarm unit and/or the immobiliser unit being responsive to the alertness signal.

Preferably the pupillometry device calculates the PUI of the person and generates a data signal indicative of said PUI value, the pupillometry comparator comparing said PUI value with predetermined, stored PUI values to generate said alertness signal.

Conveniently the device further comprises a weight detector operatively connected to a seat in the means of transport to detect said person occupying the seat, the weight detector being arranged to re-activate the immobiliser when the person is subsequently not detected as occupying the seat.

Preferably the device further comprises a display means operative to display the determined concentration.

Conveniently the device further comprises a recorder unit to record the determined concentration and/or a data signal.

Preferably the device further comprises a transmitter arrangement for transmitting data externally of the vehicle in response to the determined concentration and/or a data signal.

Conveniently the device further comprises a location means to determine the location of the means of transport and transmit a location signal externally of the means of transport via the transmitter arrangement.

Advantageously in default mode, the immobiliser unit immobilises the engine of the means of transport, the immobiliser only being deactivated in response to a specified output signal.

Preferably the device further comprises an ignition control unit operably connected to the ignition system of the means of transport to automatically start said ignition system in response to said at least one output signal.

According to another aspect of this invention there is provided a method of preventing operation of a means of transport comprising the steps of directing radiation into the eye of a person intending to take control of the means of transport, so that the radiation is internally reflected within the eye and emerges from the eye with a substantial spectral content corresponding to the spectral content of blood flowing through the retina of the eye, receiving the radiation emanating from the eye and performing a spectral analysis of the reflected radiation to determine the concentration of at least one chemical within the blood of a person, and immobilising the vehicle in response to the determination of the concentration when the concentration of the chemical is determined to be outside a permitted threshold range.

In order that the invention may be more readily understood, and so that further features thereof may be appreciated, the invention will now be described, by way of example, with reference to the accompanying drawings in which:

FIG. 1 is a schematic view of one embodiment of a security device according to the present invention.

FIG. 1 shows a security device comprising a radiation source 1, in the form of a light source emitting light, for example a fibre optic extending from a halogen lamp or laser, positioned to direct a beam of light, via a focusing lens 2, towards the eye of a person. The light may have frequencies within the visible spectrum and within the infra-red part of the spectrum and within the ultra-violet part of the spectrum, or may only emit light within a selected part of that total spectrum. It is preferred that the light is solely infra-red light, so that the light cannot actually be "seen" by a driver of a vehicle.

The radiation source may be mounted at any convenient position within a motor vehicle. The radiation source may, consequently, form part of a eye-piece assembly, conveniently positioned so that a potential driver of the vehicle may press his or her eye against the eye-piece assembly in order to release an immobiliser applied to the vehicle. The eye-piece assembly may be a telescope device to place the eye-piece over the eye. Alternatively the radiation source may be located at another position, to direct light towards the eye of the user of a vehicle whilst the vehicle is in motion.

It is preferred, wherever possible, that the light source is such that the light is focussed in the plane of the pupil of the eye, (Maxwellian View) so that the eye can be illuminated in a manner independent of pupil size. This avoids the necessity of dilating the pupil.

In the described embodiment of the invention the light source is arranged to emit pulses of illumination light, preferably in the form of a stream of pulses. Each pulse may be very short, having a duration of a few micro-seconds. It is preferred that the light is polarised.

As will become clearer from the following description, light from the radiation source will enter the eye and will be internally reflected within the eye. The eye will act as an integrating sphere, with the light repeatedly being internally reflected within the eye, with some of the light, in a diffused form, emerging from the eye. It has been found that the light emerging from the eye in this way has a substantial spectral content representative of the spectral content of blood present in the vasculatory system supplying the retina of the eye. It is for this reason that light from a "flash" on a camera which enters the eye of a subject and which is internally reflected within the eye then emerging through the pupil of the eye gives rise to the so-called "red eye" effect seen in many photographs.

The light emitted from the eye may be spectrally analysed, using sophisticated spectral analysis techniques, to determine the concentration of specific chemicals within the blood stream.

It will also be appreciated that the light illuminates the iris so that a "iris scan" may be performed.

It is preferred that the eye should be illuminated for a period of seconds, for example 9 seconds or more, the enable hippus to be measured as will be described below.

A screen 3 is provided which receives light reflected by the eye of the person and, in the embodiment shown in FIG. 1, is in the form of a CCD or CMO5 which may capture an image of at least a unique part of the eye of the person, in particular the iris, and may also capture a series of separate images, at predetermined intervals over a predetermined time period, of the pupil of the person. The screen may be polarised in such a way that the screen is not directly responsive to light reflected from the tears, tear film, cornea and/or lens of the eye.

The screen 3 generates a data signal 8 transmitting an image of the unique part of the eye and also generates a signal 27 transmitting a series of separate images of the pupil of the eye. It will be appreciated that the signals 8 and 22, including images of the a unique part of the eye and pupil respectively, are indicative of some biometric information relating to the person, which may include the appearance of the iris, the unique physical dimensions of the iris and/or the physical contours of the iris or eyeball.

The screen 3 has a number of apertures 4 (of which there are two shown in the embodiment of FIG. 1), each of which lead on to a respective light guide 5, which may be in the form of an optical fibre. The light guides 5 are all connected to analysing means in the form of a spectral analyser 6, which is configured to receive light reflected from the eye of the person, travelling along the guides 5. The spectral analyser 6 performs a spectral analysis of the diffuse reflected light to produce a data signal 7 indicative of the spectral components of the reflected light. Thus, data signal 7 may indicate the intensity of the light of each specific wavelength present in the light, or may indicate the relative intensities of light of pre-determined specific wavelengths. In a preferred embodiment, the spectral analyser 6 may execute an algorithm to effectively 'select' the specific characteristic wavelengths indicative of the amount of certain constituents of the blood such as, for example, alcohol or other drugs, and determine the intensity of the reflected light at each of the selected wavelengths.

It is preferred that the spectral analyser should be capable of performing a fourier transform analysis of the data signal, with that analysis preferably being carried out in the near-infra-red spectrum.

Fourier transform near infra-red spectroscopy has been carried out, in an absorption spectrometers, for a number of years, and it is known that this form of spectroscopy can provide a very powerful analysis tool for analysing the concentration of specific chemicals within a sample.

It will be appreciated that the proportion of the light of each specific wavelength present in the diffuse reflected light will be dependent upon absorption and emission of light by the constituents of the blood at the back of the person's eye, including chemical elements and substances present within the cells of the eye and, in particular, within the bloodstream in the proximity of the eye of the person. Thus, the data signal 7 representative of the spectral components of the reflected light is, also, representative of biometric information relating to that person, in that it is representative of constituents of the blood of the person, including, in particular, the concentration of certain chemical elements and substances within the blood at the back of the eye of the person (in turn representative of the amount of these chemical elements and substances within the bloodstream of the person), in particular alcohol or other drugs, and also glucose.

Referring again to the specific embodiment of the FIG. 1, the device is also provided with a pupillometry device 26 which receives a signal from the screen 3 in the form of a series of separate images of the pupil of the person determined at intervals over a predetermined time period and which performs an analysis of certain biometric information within the series of separate images to generate a data signal 22 in the form of a signal representing certain biometric information relating to the person which is indicative of the level of mental alertness of the person. In the preferred embodiment, the pupillometry device 26 analyses the fluctuations in pupil size over the set time period by recording measurements of pupil size over the set period and performing a suitable algorithm to calculate, in conventional manner, the Pupillary Unrest Index (PUI) for the person, known to be an indicator of the mental alertness of the person. In such a case, the output signal generated by the pupillometry device will include information concerning the calculated value of the PUI for the person.

Here it is to be understood that the iris of a typical eye exhibits hippus, that is to say continuous small changes in the area of the pupil. Should a pupil remain at a fixed size over a long period of time, then hippus is not present, and it is quite possible that the iris is a "false" iris which may be present in the form of a contact lens provided to "fool" the iris scanner. Thus the pupillometry device is also configured to provide an output indicative of the absence of hippus, which will prevent the described arrangement providing a confirmation of the identity of the scanned iris.

It will be appreciated that the series of separate images may be captured by the screen 3 at any suitable intervals over any suitable time period which would allow the relevant analyses of biometric information represented in the separate images, for example measurement of people's eyes and subsequent calculation of the PUI of the person, to be performed. Preferably, the series of separate images are captured at equal predetermined intervals over a predetermined time period, for example at a frequency of around 25 to 75 hertz for a time period of 60 seconds. It is to be understood that the selection of a suitable time period for recording the series of separate images is a "trade-off" between the accuracy of the analysis carried out by the pupillometry device 26 (which will be higher when a longer time period is used) with the inconvenience of the person being delayed by having to wait before they can take control of the vehicle (if they are eventually authorised to do so).

The determination of PV1 cold be a continuous assessment using technology now utilised in conjunction with head-up displays to monitor the eyes of the vehicle operator.

It is preferable that the series of separate images captured by the screen 3 are infrared images.

It will be appreciated that the screen 3, apertures 4, light guides 5, spectral analyser 6 and pupillometry device 26 together constitute a receiver arrangement, indicated schematically at 9 in FIG. 1, to receive light reflected from the eye of the person and generate a data signal (and, indeed, in the embodiment FIG. 1, three separate data signals 7, 8 and 22) indicative of biometric information relating to the person (which, in the case of data signals 8 and 22 is in the form of information concerning the physical characteristics or behaviour of the eye of the person and, in the case of data signal 7, is in the form of concentrations of certain chemical elements and substances within the bloodstream of the person respectively).

It is to be recalled that the radiation source 1 in the described embodiment operates to provide repeated pulses of light. The receiver arrangement is preferably configured to provide an output only at a predetermined selected time relative to each of the pulses of light. It is preferred that the selected period of time should be at the end of each pulse of radiation or shortly after the end of each pulse of radiation, so that radiation which is actually reflected from the cornea or lens of the eye is not detected by the receiver, but light which has been multiply reflected within the eye, and which thus carries a substantial spectral content related to the blood flowing through the retina at the back of the eye is received by the receiver.

One advantage of using pulsed light is that the risk of light energy heating or otherwise damages the retina of the eye.

Referring again to FIG. 1, the spectral analyser 6 and screen 3 are each electrically connected to a comparator arrangement, indicated schematically at 10 in FIG. 1. The comparator arrangement 10 includes a spectral comparator 11, having an associated memory 12 which stores predetermined data signals corresponding to the spectral components anticipated to be present in light reflected from the eye of a person who has not used any drug or alcohol, or who has used a drug or alcohol but only to an acceptable level. Alternatively the memory may store signals corresponding to the spectral components anticipated to be present in light reflected from the eye of a person who has used a drug or alcohol to an unacceptable level.

The spectral comparator 11 performs a comparison of the relevant spectral component or spectral data contained within the data signal 7 from the spectral analyser with the corresponding spectral component or spectral data relating to a suitable predetermined, stored signal in the memory 9 to provide an output signal 13. In a preferred embodiment, where the data signal 7 is in the form of a signal transmitting certain spectral data derived from the reflected light, such as the relative intensity of the reflected light at only selected wavelengths, then the memory 9 need only contain data concerning the relevant intensity at all possible specified wavelengths.

Of course, it is to be understood that the comparator arrangement may operate in various different ways, to achieve the end result that an appropriate signal is generated when the spectral content of the light emanating from the eye is indicative of the fact that the blood within the eye has an unacceptable drug or alcohol content.

Conveniently, the output signal 13 may be one of two possible output signals, for example an "accept" signal indicative of non-use, or only acceptable use, of a drug or alcohol or, alternatively, a "reject" signal indicative of an unacceptably high concentration of a particular drug or alcohol in the bloodstream. In such a case, the output signal 13 may conveniently be provided in the form of a binary signal with the "accept" signal being represented by a binary "one" and "reject" signal being represented by a binary "zero", or vice versa. The output signal may also contain a quantitative indication of the actual concentration of a particular drug or alcohol in the bloodstream.

Whilst, in the present embodiment, the device operates primarily to provide an output signal dependent upon the level of alcohol or other drug within the bloodstream of the person, it is to be noted that the output signal might equally be dependent upon the level or concentration of other constituents of the blood of the person which may be determined by spectral analysis of relevant spectral components, such as, for example, glucose (which, particularly in the case of a diabetic, may be at an unacceptably low level or may be at an unacceptably high level for that person to safely take control of a vehicle). Thus, the associated memory 12 may alternatively, or additionally, store predetermined data signals corresponding to the spectral components anticipated to be present in light reflected from the eye of a person having a normal, or unacceptably low, or unacceptably high blood glucose level so that the output signal 16 is an "accept" signal only if the blood glucose level of the person is determined to be at an acceptable level. In the same way, it is envisaged that, by storing the relevant predetermined data signals within the associated memory 12, the output signal 16 might be dependent upon other constituents of the blood being determined to be at an "acceptable" level or concentration.

In addition to the spectral comparator 11, the comparator arrangement 10 also comprises a pupillometry comparator 23 having an associated memory 24 which stores predetermined data signals in the form of signals representing certain selected biometric information which is indicative of the mental alertness of the person. In the preferred embodiment the biometric information is in the form of PUI data comprising at least one PUI value, and preferably several PUI values, indicative of a particular level, or varying degrees of, mental alertness. The pupillometry comparator 23 receives the data signal 22, containing a calculated PUI for the person and compares this value with one or more of the stored PUI values in the associated memory 24 to assess whether or not the PUI value calculated for the person is indicative of an acceptable level of mental alertness and, thus, provide an output signal 25, in the form of a "reject" or "accept" signal indicating whether or not the person is sufficiently mentally alert to take control of the vehicle. Again, the output signal 25 may conveniently be in the form of a binary signal.

In the particular embodiment shown in FIG. 1, the comparator arrangement 10 also comprises the optional feature of a recognition device, in the particular form of an iris recognition device 14. The iris recognition device 14 has an associated memory 15 which stores predetermined signals in the form of images formed by light reflected from the eye of the or each person who has been specified as being "acceptable", for example the owner or authorised driver of a motor vehicle, or a person who is authorised to take control of a particular means of transport.

The iris recognition device 14 receives the data signal 8, i.e. in this case the image of the iris of the person, captured by the CCD screen 3, and compares specified unique biometric information within the image captured by the screen 3, for example the appearance of the iris, or physical characteristics of the iris, with corresponding unique biometric information within each of the images stored in the memory 15 to verify whether or not the biometric information is a match and, consequently, whether or not signal 8 corresponds to the eye of a person having an "acceptable" identity subject, of course, to hippus being present. Iris recognition device 14 thus provides an output signal 16 which indicates whether or not the image captured by the CCD screen 3 is of an eye belonging to an "acceptable" person. Again, conveniently the output signal 16 may be in the form of a binary signal as in the case of output signal 13.

The image captured by the CCD screen 3 and transmitted, via data signal 8, to the iris recognition device 14 is preferably in the form of a visual image (i.e. formed from "visible" light) and, in such a case, it is envisaged that the screen 3 may be split into two distinct parts, with one part recording a visual image to the transmitted to the iris recognition device 14, and the remaining part recording a series of separate infrared images to be transmitted to the pupillometry device 26.

The comparator arrangement 10 is, in turn, operatively connected to an immobiliser unit 17 which receives each of the output signals 13, 16 and 25 from the spectral comparator 11, iris recognition device 14 and pupillometry comparator 23 respectively. The immobiliser unit 17 is configured so that, by default, it operates to immobilise a component essential to normal operation of the vehicle in which the device is mounted, preferably a component essential to starting the engine, as indicated schematically in FIG. 1 (19). In operation, the immobiliser unit 17 receives each of the output signals 13,16 and 25 from the comparator arrangement 10 and operates to remove the default immobilisation of the essential components of the motor vehicle only in the case where each of the output signals 13, 16 and 25 are "accept" signals, as described above. Thus, in the case where either of the output signals 13, 16 or 25 are "reject" signals, representing respectively an unacceptably high concentration of a particular drug in the bloodstream of the person, non-verifiable identity or insufficient mental alertness, the immobiliser unit remains in its default mode, with a component essential to normal operation of the vehicle being immobilised so that the particular person cannot take control of, or preferably even "start", the vehicle concerned.

In the particular embodiment shown in FIG. 1, the device also comprises an alarm unit 18, which receives the output signal 13 and 16 and in the case where either one of these signals are "reject" signals, generates an audible alarm to provide a warning to persons in the vicinity of the vehicle that the person to whom the output signal corresponds is not a person authorised to take control of that particular vehicle, either because his or her identity cannot be verified (in the case of "reject" signal 16) or because the level of alcohol or other drugs in the bloodstream is deemed to be unacceptably high (represented by a "reject" output signal 13). It will be envisaged that the alarm unit 18 may be provided in place of the immobiliser unit 17 but, more preferably, the alarm unit 18 is provided as a secondary additional warning system.

As shown in FIG. 1, the comparator arrangement 10 may also be electrically connected to a display means 21, which may be in the form of a VDU for example, to display a result corresponding to the output signals 13 and 16. A display means may be particularly useful in a situation where the output signal 13 provides a quantitative indication of blood alcohol content of the person intending to take control of the vehicle, in which case that person may be provided with information, via display means 21, as to how long it will be before he or she may have an acceptably low blood alcohol content.

It will be appreciated by the person skilled in the art that the precise form of the comparator arrangement 10 may be varied; for example, the memories 15, 12 and 24 may be incorporated into a single memory unit (not shown).

In operation of the device a person intending to drive the motor vehicle positions one or both of their eyes to receive light from the radiation source 1. If the radiation source 1 forms part of an eye-piece assembly, then the eye or eyes of the person must be located in front of the eye-piece assembly. On the other hand, if the radiation source is at another position, then the person must occupy a normal driving position within the vehicle.

Light reflected by the eye of the person is received by the receiver arrangement 9 and forms an image of at least a portion of the iris on the CCD screen 3 which is transmitted, via data signal 8, to the iris recognition device 14. At the same time, the screen 3 records a series of images of the pupil of the person and transmits the series, via data signal 22, to the pupillometry comparator 23. Finally, reflected light incident upon the apertures 4 in the screen 3 passes along the light guides 5 (for example through a series of internal reflections where the light guide is an optical fibre) and into the spectral analyser 6. The spectral analyser 6 performs a spectral analysis of the reflected light which has been multiply reflected internally within the eye and, subsequently, outputs data signal 7 which is indicative of the spectral components of the reflected light and, consequently, the concentration of the blood alcohol level within the person's bloodstream.

Data signals 7, 8 and 22 subsequently pass into the spectral comparator, iris recognition device 14 and pupillometry comparator 23 respectively, where they are compared to the predetermined signals stored within the respective memories 12, 15 and 24 to provide output signals 13, 16 and 25, the form of which will depend, respectively, on the blood alcohol content within the bloodstream of the person, identity of that person and mental alertness of the person respectively. Thus, taking the specific example wherein the person is a person authorised to take control of the vehicle (so that a pre-recorded image of the iris of the person has been stored in the memory 15), is sufficiently mentally alert, but he or she has an unacceptably high blood alcohol level within the bloodstream (so that the data signal 7 is indicative of a set of spectral components which do not correspond to a predetermined acceptable set of spectral components), the output signals 16 and 25 will be an "accept" signal but the output signal 13 will be a "reject" signal. In such a case the immobiliser unit 17 will then remain in the default mode so that a component essential to the operation of the vehicle is immobilised and, consequently, the person cannot take control of, or preferably even "start", the vehicle. In addition, the alarm unit 18 will operate to provide an audible alarm warning to passers by that the person attempting to take control of the vehicle is, in some way, not authorised to do so.

It will be appreciated, from the above discussion, that in the case where the person has an acceptably low concentration of alcohol within his or her blood, but is either not a person being authorised to take control of the vehicle or not a person being sufficiently mentally alert, the output signal 13 will then be an "accept" signal, but the output signals 16 and 25 will become "reject" signals, so that, similarly, the immobiliser will remain in the default mode and the alarm will again provide an audible warning to passers-by.

Indeed, only where the person is a person who is authorised to take control of the vehicle, a person who is sufficiently mentally alert and a person having an acceptably low blood alcohol content will the output signals 13, 16 and 25 be "accept" signals. In such a case, the immobiliser unit will switch from its default mode and remove the immobilisation of the components essential to operation of the vehicle (which had been previously immobilised), so that the person can then proceed to start the engine of the vehicle and fully operate the vehicle. No alarm would, of course, be generated by the alarm unit in such circumstances because none of the output signals 13, 16 or 25 would be "reject" signals.

Where the radiation source is positioned to provide radiation to the eyes of the driver of the vehicle at all times, should the driver become intoxicated whilst driving, or should the blood glucose level of the driver reach an unacceptable level while the driver is driving, the security device will be able to determine that fact and may respond appropriately. For example, the security device may gradually apply the brakes of the vehicle until the vehicle comes to a complete standstill or, alternatively, the security device will be arranged so that, if the vehicle does come to a standstill, the engine of the vehicle is turned off to prevent the vehicle being driven by a driver in an unfit condition.

In one embodiment in which the radiation source forms part of an eye-piece assembly the device may also include a weight detector, operatively coupled to a vehicle seat to be occupied by the person intending to take control of the vehicle, in order to detect the presence of the person in the seat by detecting the weight of that person on the seat. The weight detector is operatively coupled to the immobiliser unit such that, in operation, once the weight detector has detected the presence of the person intending to take control of the vehicle in the seat, any subsequent vacation of the seat by the person will trigger the weight detector to provide a trigger signal to the immobiliser unit causing the immobiliser to re-activate, thus immobilising the vehicle. It will be appreciated that the weight detector thus operates to prevent a person who is authorised to take control of the vehicle, is mentally alert and has an acceptably low concentration of a drug or alcohol from nevertheless allowing a person who is not authorised and/or mentally alert, or who has unacceptable levels of a drug or alcohol in their blood, to drive the vehicle. Specifically, the weight detector prevents a person from using his or her eye to de-activate the immobiliser and then subsequently vacating the seat and allowing an "unauthorised" person to take control of the vehicle.

Optionally, the weight detector may be provided with a timer which delays the trigger signal to avoid unintentional reactivation of the immobiliser when a person merely shifts their weight on the seat whilst driving or vacates the seat for a very short space of time.

In a further embodiment, the security device may be provided with a data recorder unit (not shown), preferably in the form of a sealed, tamper-proof "black box" recorder, which receives the data signals generated by the receiver arrangement and/or the output signal generated by the comparator arrangement, and records data contained within the data signal and/or output signal, for example, by recording the entire data signal and/or output signal itself or by recording specific data contained within the data signal and/or output signal such as, for example, biometric information relating to a person. The recorded data may then be retrieved from the data recorder unit at a later date.

In another preferred embodiment, it is envisaged that the security device may also be operatively connected, via an ignition controller unit (not shown), to the ignition system of the vehicle such that transmission of "accept" output signals 13, 16 and 25 to an ignition controller unit will result in the ignition controller automatically starting the vehicle ignition, without the need for the driver to manually start the ignition.

In a yet further embodiment (not shown), it is envisaged that the device will be provided with a transmitter arrangement which may transmit data externally of the motor vehicle in response to the data signal and/or output signal, for example to a local police station having an "open" receiver. Such data may include, for example, the registration number of the vehicle, the colour of the vehicle, the make and model of the vehicle which would allow the police to track the details of the vehicle. The data may also include biometric information relating to the person and, in particular, an image of the iris of the person which would allow comparison with images of irises stored on a police database.

Preferably, the transmitter arrangement is provided in conjunction with a location means to determine the location of the vehicle and provided a location signal, which may also be transmitted to the police station via the transmitter arrangement.

When used in this Specification and Claims, the terms "comprises" and "comprising" and variations thereof mean that the specified features, steps or integers are included. The terms are not to be interpreted to exclude the presence of other features, steps or components.

The features disclosed in the foregoing description, or the following Claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. A security device for a means of transport comprising:
   a radiation source to direct radiation into an eye of a person intending to take control of the means of transport so that the radiation is internally reflected within the eye and emerges from the eye with a substantial spectral content corresponding to the spectral content of blood flowing through the retina of the eye;
   a receiver arrangement for receiving radiation emanating from the eye of the person and to perform a spectral analysis of the reflected radiation to determine the concentration of at least one chemical within the blood of the person; and
   an alarm unit for generating an alarm and an immobilizer unit for immobilizing the means of transport, wherein the alarm unit and immobilizer unit are responsive to the determination of concentration when the concentration of the chemical is outside a permitted threshold range.

2. The security device according to claim 1, wherein the receiver arrangement is configured to form a spectral analysis of the reflected radiation to determine the concentration of alcohol within the blood of the person, the alarm unit being configured to generate an alarm and the immobilizer unit being configured to immobilize the means of transport in response to a determination of a concentration of alcohol concentration in excess of a predetermined threshold.

3. The security device according to claim 1, wherein the receiver arrangement is configured to perform a spectral analysis of the reflected radiation to determine the concentration of glucose within the blood of the person, the alarm unit being configured to generate an alarm and the immobilizer unit being configured to immobilize the means of transport in response to the concentration of glucose being above a predetermined threshold or beneath a second permitted threshold.

4. The security device according to claim 1, wherein the radiation source is arranged to provide radiation in sequential pulses, the receiver arrangement being configured to perform said spectral analysis on reflected radiation received during a selected time period relative to each said pulse so as to reduce the proportion of light reflected from tears, tear film, cornea or lens of the eye.

5. The security device according to claim 4, wherein the receiving means is configured to perform the spectral analysis during a time period which commences at the end of or shortly after the end of each said pulse.

6. The security device according to claim 1, wherein the radiation source is configured to focus the radiation in the plane of the pupil of the eye.

7. The security device according to claim 1, wherein the radiation source is a source of polarized light and wherein the receiver arrangement is also polarized, the polarization being such that the receiver will receive only a minimum of light reflected from tears, tear film, cornea, or lens of the eye.

8. The security device according to claim 1, wherein the receiver arrangement is configured to generate at least one data signal indicative of additional biometric information relating to the person, the device further comprising a comparator arrangement to compare said data signal with corresponding predetermined signals stored in a memory and to generate at least one output signal, the alarm unit and the immobilizer unit being responsive to said output signal.

9. The security device according to claim 8, wherein the comparator arrangement includes a recognition device which receives a data signal in the form of an image of at least part of the eye of the person and compares the image with a corresponding predetermined image stored in a memory to verify the identity of the person, wherein the at least one output signal is in the form of a signal indicative of said verification.

10. The security device according to claim 9, wherein the image is an image of at least a portion of the iris of the person.

11. The security device according to claim 10, wherein the receiver arrangement is configured to determine hippus of the iris of the eye, and to inhibit generation of said output signal if hippus is not, present.

12. The security, device according to claim 8, wherein the receiver arrangement device further comprises a pupillometry device for receiving a pupillometry data signal in the form of a series of separate images of the pupil of the person formed by said reflected radiation over a set time period, the pupillometry device being configured to analyze specified information within the pupillometry data signal and generate an output signal in the form of an alertness signal indicative of the level of said mental alertness of said person, wherein when the alertness signal is beneath an acceptable threshold, the alarm unit and the immobilizer unit being responsive to the alertness signal.

13. The security device according to claim 12, wherein the pupillometry device calculates the PUI of the person and generates a data signal indicative of said PUI value, the pupillometry comparator comparing said PUI value with predetermined, stored PUI values to generate said alertness signal.

14. The security device according to claim 1, wherein the device further comprises a weight detector operatively connected to a seat in the means of transport to detect said person occupying the seat, the weight detector being arranged to re-activate the immobilizer when the person is subsequently not detected as occupying the seat.

15. The security device according to claim 1, wherein the device further comprises a display means operative to display the determined concentration.

16. The security device according to claim 1, wherein the device further comprises a data recorder unit to record the determined concentration or a data signal representative thereof.

17. The security device according to claim 1, wherein the device further comprises a transmitter arrangement for transmitting data externally of the means of transport in response to the determined concentration or a data signal representative thereof.

18. The security device according to claim 17, wherein the device further comprises location means to determine the location of the means of transport and transmit a location signal externally of the means of transport via the transmitter arrangement.

19. The security device according to claim 1, wherein in a default mode, the immobilizer unit immobilizes the engine of the means of transport, the immobilizer only being deactivated in response to a specified output signal.

20. The security device according to claim 1, wherein the device further comprises an ignition control unit operably connected to an ignition system of the means of transport to automatically start said ignition system in response to said at least one output signal.

21. A method of preventing operation of a means of transport comprising the steps of:
- directing radiation into an eye of a person intending to take control of the means of transport so that the radiation is internally reflected within the eye and emerges from the eye with a substantial spectral content corresponding to the spectral content of blood flowing through the retina of the eye;
- receiving the radiation emanating from the eye and performing a spectral analysis of the reflected radiation to determine the concentration of at least one chemical within the blood of the person; and
- generating an alarm and immobilizing the means of transport in response to the determination of the concentration when the concentration of the chemical is determined to be outside a permitted threshold range.

* * * * *